(12) United States Patent
Srocka et al.

(10) Patent No.: US 9,217,633 B2
(45) Date of Patent: Dec. 22, 2015

(54) INSPECTION ARRANGEMENT

(71) Applicant: HSEB Dresden GmbH, Dresden (DE)

(72) Inventors: Bernd Srocka, Berlin (DE); Ralf Langhans, Dresden (DE)

(73) Assignee: HSEB DRESDEN GmbH, Dresden (DE)

( * ) Notice: Subject to any disclaimer, the term of this patent is extended or adjusted under 35 U.S.C. 154(b) by 0 days.

(21) Appl. No.: 14/395,493

(22) PCT Filed: Apr. 5, 2013

(86) PCT No.: PCT/EP2013/057180
§ 371 (c)(1),
(2) Date: Oct. 19, 2014

(87) PCT Pub. No.: WO2013/156323
PCT Pub. Date: Oct. 24, 2013

(65) Prior Publication Data
US 2015/0124245 A1 May 7, 2015

(30) Foreign Application Priority Data
Apr. 19, 2012 (DE) .......................... 10 2012 103 428

(51) Int. Cl.
*G01N 21/00* (2006.01)
*G01B 11/14* (2006.01)
(Continued)

(52) U.S. Cl.
CPC .............. *G01B 11/14* (2013.01); *G01B 11/026* (2013.01); *G01B 11/26* (2013.01); *G01N 21/9501* (2013.01); *G01N 21/211* (2013.01); *G01N 2201/062* (2013.01)

(58) Field of Classification Search
CPC .............. G01J 3/02; G01J 3/513; G01J 3/51; G01N 15/1459; G01N 21/65

USPC .......................................................... 356/73
See application file for complete search history.

(56) References Cited

U.S. PATENT DOCUMENTS 4,230,940 A    10/1980 Minami et al.
5,039,868 A *   8/1991 Kobayashi et al. ...... 250/559.08
(Continued)

FOREIGN PATENT DOCUMENTS

DE    19816974 C1    1/2000
JP    S59/203906 A   11/1984
(Continued)

OTHER PUBLICATIONS

PCT Application PCT/EP2013/057180; Filing date Apr. 5, 2013; HSEB Dresden GmbH; International Search Report mailed May 24, 2013.

*Primary Examiner* — Tarifur Chowdhury
*Assistant Examiner* — Md Rahman
(74) *Attorney, Agent, or Firm* — Thorpe North & Western, LLP

(57) ABSTRACT

The invention relates to an arrangement for analyzing an at least partially reflective surface of a wafer or other objects, containing a holder for holding the object; an inspection arrangement arranged at a distance in the region in front of the surface to be analyzed; and a measurement arrangement for determining the distance and/or inclination of the surface for the inspection arrangement; characterized be a radiation source, the radiation of which is directed towards the surface to be analyzed at an angle; and a spatially resolving detector for receiving the radiation from the radiation source that is reflected from the surface to be analyzed, wherein the radiation source and the detector are arranged outside the region necessary for the inspection between the inspection arrangement and the surface to be analyzed.

12 Claims, 4 Drawing Sheets

(51) Int. Cl.
*G01B 11/26* (2006.01)
*G01B 11/02* (2006.01)
*G01N 21/95* (2006.01)
*G01N 21/21* (2006.01)

(56) References Cited

U.S. PATENT DOCUMENTS

| | | | |
|---|---|---|---|
| 5,064,291 A * | 11/1991 | Reiser | 356/625 |
| 5,218,415 A | 6/1993 | Kawashima | |
| 5,825,469 A | 10/1998 | Nam et al. | |
| 6,091,499 A | 7/2000 | Abraham et al. | |
| 2001/0012107 A1 * | 8/2001 | Toh | 356/601 |
| 2002/0053643 A1 | 5/2002 | Tanaka et al. | |
| 2009/0207408 A1 | 8/2009 | Liphardt et al. | |
| 2010/0277748 A1 | 11/2010 | Potapenko | |
| 2011/0090547 A1 * | 4/2011 | Sugiyama et al. | 358/505 |

FOREIGN PATENT DOCUMENTS

| | | |
|---|---|---|
| WO | WO 02/079760 A2 | 10/2002 |
| WO | WO 2007/025398 A1 | 3/2007 |

* cited by examiner

INSPECTION ARRANGEMENT

TECHNICAL FIELD

The invention relates to an assembly for inspecting an at least partly reflecting surface of a wafer or other object.

Furthermore, the invention relates to an inspection method for inspecting an at least partially reflecting surface of a wafer or another object with an inspection assembly positioned spaced apart in the range before the inspected surface, the method used for determining the distance and/or inclination of the surface with respect to the inspection assembly.

In different branches of the industry flat products are inspected with optical methods regarding their properties. In semiconductor- and solar cell industry these are amongst others wafers. Wafers are discs of semiconductor-, glass-, sheet- or ceramic materials. The exact determination of the surface position of the sample during various inspection steps is important for the correct performance of the inspection itself and for the correct interpretation of the measuring results. The position of the surface of the sample is determined in particular by its height and its inclination. The term "height" is defined here as the distance to the inspection assembly.

Exact knowledge about the generated layers and surfaces is required for the production control and the quality checking. Various inspection methods are used for such purposes. The inspection methods are used to measure material- and structural parameters as well as layer properties of the uppermost layer or several of the upper layers. A plurality of methods requires the very exact control of the distance of the surface to the inspection assembly and the inclination of the surface at the place of inspection with respect to characteristic axes of the inspection assembly.

Examples for methods processing the information about the distance and inclination of the sample relative to the measuring head are ellipsometry, scatterometry, reflectometry, optical inspection, inspection methods using different electromagnetic radiation and ultra sound sensors. Apart from the measured parameter itself the measured signals generated with such methods depend on the above mentioned two parameters. All methods require a sample laying in a plane relative to the normal axis of the inspection system. The requirements with respect to the inclination for ellipsometry, reflectometry and scatterometry are particularly high. Generally, the methods require much space directly above the inspection location for the inspection apparatus. In particular, there are optical components used with a large opening angle which require large diameters close to the surface of the sample. The spacial conditions limit the options to determine the distance and the inclination of the sample at the location of the inspection.

PRIOR ART

It is known to carry out ellipsometric measurements for nondestructive layer analysis. The sample is illuminated with polarized light. The light is reflected at the boundaries between the layers or transmitted and finally detected. The properties of the layers are determined by the change of the polarization state of the detected light. Such measured values depend very much on the focus position and the inclination of the surface of the sample.

Scatterometry is used for the inspection of structural properties. With scatterometry the response signal of a light beam is inspected which is incident at different angles. Additionally or alternatively, light with different wavelengths can be used. By model calculation the structure parameters are adapted to the response signal.

The measurements require the use of optical systems with a large aperture for a good resolution and high reproducibility. This means that the light is incident on the sample surface has an inclination as flat as possible. Devices for the exact determination of the distance to the sample and the inclination also require a high aperture. The assemblies can normally not be carried out in the same optical assembly for use as the measuring optics or only by interfering with the measurement.

There are autofocus systems known imaging one or more laser beams through the observation objective of the inspection system or an additional objective onto the sample. The radiation is directed outside the optical axis. It is reflected at the sample surface and directed to a spatially resolving detector back through the same objective optical assembly. Such a spatially resolving detector is, for example, a CCD line detector. Accordingly, the returning radiation is a mirror image with respect to the optical objective axis. It generates a signal in a well-defined position at the detector. A certain position corresponds exactly to the focus position defined by the distance between the objective and the sample surface, where the sample is positioned in the focus of the optical assembly. A different distance causes a corresponding shift of the signal on the CCD line detector. The focus position can be re-adjusted.

Furthermore, systems are known which image a line pattern onto the sample and detect the returning beams on an inclined detector surface. The reflected line pattern is analyzed regarding its contrast. The position with the highest contrast indicates the focus position.

With both methods the radiation is directed through the imaging optical assembly of the inspection system. It is, therefore, necessary to insert additional components into the optical path and remove them therefrom. Such elements may interfere with the measurement itself.

An optical assembly is necessary in addition to the ellipsometer arms in an ellipsometer according to known methods. Such optical assembly also requires a large aperture and accordingly much space directly above the measuring position. Thereby, the determination of the position of the sample surface is limited.

WO 02079760A2 (Norton) discloses a scatterometer and a spectroscopic ellipsometer. Such assembly is used to measure the structure features of a wafer.

US 2009 207408 (Liphardt) discloses an assembly for adjustment with an essentially perpendicular beam.

DE 198 16 974 C1 shows an ellipsometer for the inspection of flat samples. The ellipsometer uses a light source arranged on the side the radiation of which is incident on the sample with a flat angle and in the direction of a conus polarimeter. A sample position determining system is arranged above the sample. A first beam of the laser is directed to the sample through a partly transmitting mirror and the laser beam reflected by the sample is detected with a detector. A second beam passes the partly transmitting mirror and is directed to the sample by means of another mirror. This beam is incident on the sample with an angle.

DISCLOSURE OF THE INVENTION

It is an object of the invention to provide an assembly and a method according to the above mentioned kind which recognize differences of the inclination and the height during inspection of surfaces with simple measures without interfering with the inspection.

According to an aspect of the present invention this object is achieved with the features of claim 1.

The assembly according to the present invention is based on the finding that the position of the beam (radiation) reflected by the surface of the detector varies if the surface of the object is inclined or its height is changed. For example, the detector detects the beam in the range with a larger distance from the surface if the sample is lifted or inclined towards the radiation source. If the sample is lowered or inclined in the direction of the detector the detected beam on the detector surface moves in the direction of the inspected surface. If the sample is inclined to the left about the projected axis of the connecting line between the radiation source and the detector the beam also moves towards the left on the detector. The analogue applies with the inclination towards the right.

The position of the beam on the detector reflected by the inspected surface is, therefore, a measure for the distance or the inclination of the inspected surface. Absolute values can be determined by suitable calibration.

The method uses the possibility to measure close to the point of inspection with distant devices, i.e. a radiation source and a detector. A range which is required for the inspection is present between the inspection assembly and the inspected surface. Radiation is, for example, directed through such range. According to the invention there are no devices present in such range. The radiation source and the detector are positioned outside such range.

Two radiation sources with a corresponding detector each are provided at different positions, in particular, the radiation sources be are provided with the corresponding detector in a crossing arrangement with respect to each other. The use of two independent measurements allow the simultaneous determination of the height and the inclination of the surface of the object. The angle between the two paths of rays can be, for example, a right angle.

The radiation sources each emit a collimated beam at a flat angle onto the inspected surface. The point of incidence is selected such that the optical assembly of the inspection system is not interfered with for its tasks. The point of incidence is, therefore, slightly beside the actual inspection point. It is not required for carrying out the invention that both beams are incident on the same point of the inspected surface. Also, the incident angles must not be identical. The beams are reflected at the inspected surface. The reflected beams are detected by the corresponding detector. A beam reflected by a surface which is shifted in height or inclined is incident on the space resolving detector at a different place and thereby indicates the changed position of the inspected surface.

From the two positions of the points of incidence on the detector the effects of the height change of the inspected surface and the inclination can be unambiguously separated from each other. There is only a change of height if the points of incidence for the beams on both detectors lay on the line intersecting the detector plane and the plane perpendicular to the emitted beam. If both points lay above the normal point of incidence the surface is too high. If they lay below the surface is too low.

Since both radiation source-detector-pairs form an angle, each inclination of the sample will cause a sideways shift of the point of incidence on at least one of the two detectors.

The reason for this is that the two projected connecting lines between the radiation source and the detector each define a theoretical rotation axis. As such two rotation axes will not extend parallel due to the angular arrangement the sample cannot generate a sideways shift of the reflected beam with respect to both axes only if it extends exactly in a horizontal direction.

Means may be provided for determining the height and/or inclination of the inspected surface from the position of the reflected radiation on the detector. Such means may comprise, for example, a computer for calculating absolute values from the measured values. For example, the distance between a point on the inspected surface and a defined point at the inspection assembly may be determined using a suitable computer program or by comparison with a calibration curve. The inclination of the inspected surface with respect to the horizontal line or the like may be determined in a similar way.

Additionally or alternatively, the support or the object in the support may be moveably mounted and the inclination and/or height of the inspected surface may be adapted to be adjusted in such a way that a desired position of the reflected radiation on the detector is achieved. There are applications where an absolute determination of the height or the inclination is not necessary at all. It is sufficient to control the position of the surface to a set value. Such a set value can be defined by a point on the detector surface or the detector surfaces, respectively. The position of the object is tracked in order to maintain the set value during inspection.

According to the invention, the angle at which the radiation is directed from the radiation source to the inspected surface is in the range between 45° and 85° relative to the surface normal of the inspected surface. In other words; the beam is incident on a horizontal surface at a flat angle, for example, almost horizontal. The beam will then fit in the intermediate space between the inspection assembly and the inspected surface. Radiation sources and detectors may then be positioned outside such intermediate space and will not interfere with the inspection of the surface itself.

The radiation source may be selected differently depending on the application and the economic requirements.

The radiation source may be formed by a Laser with well collimated beam, for example a laser diode or by a LED equipped with a collimator optics or by a radiation source with an extended wavelength spectrum adapted to detect interferences at repeating structures of the inspected surface.

If there are repeating grating structures present on the inspected surface the diffraction of the beam at such grating and the resulting splitting-up to beam portions of the diffraction orders must be considered. This can be achieved by different measures. For one thing, a white radiation source or a radiation source with a sufficiently large wavelength spectrum can be used instead of monochromatic light. An intensity distribution will be generated on the detector in the form of an interferogram. The highest maximum is formed by the zeroth diffraction order because all colors of the light contribute. The other maxima of the diffraction will be at a different location on the detector for each wavelength and therefore form a more or less flat background. On the other hand the maximum with the highest intensity may also be searched for with a monochromatic light source because it is always generated by the zeroth diffraction order. The higher diffraction orders symmetrically lay around the zeroth order and have smaller intensities depending on the structure of the grating arrangement.

If a Laser is used for the assembly it is advantages not to use a correction of the astigmatism and instead direct the beam in a transversal direction whereby the semimajor of the beam ellipse extends lateral with respect to the incident plane of the sample. The semiminor is extended in the point of incidence by the flat illumination angle. Thereby, the beam is reflected by the inspected surface with much smaller ellipticity.

It is advantageous if the portion of the inspected surface illuminated by the incident beam is large enough to detect a reflection averaged over possible structures on the inspected surface. Thereby, effects of roughness will be reduced. The proportion of the illuminated surface and the size of the structure can be easily adjusted by collimation and the distance between the radiation source and the inspected surface.

The detector may be a Charge-Coupled-Device (CCD), a CMOS or another array detector with high spacial resolution or the detector comprises position sensitive photodiodes or quadrant diodes. Preferably, the used detectors are electrooptical array cameras detecting a high resolution image of the reflected image profile selected according to the respective use requirements. The center of gravity of the detected beam image can be determined with known image processing algorithms and thereby the local position of the beam center can be read out with very high accuracy. Alternatively, simpler recording systems, such as, for example, quadrant diodes or position sensitive photodiodes can be used. Quadrant diodes are an assembly of four photodiodes. Position sensitive photodiodes are large area photodiodes where the center location of gravity of the signal is determined by a generated voltage difference of the signals taken at the edges of the active area.

Such known detectors all have the purpose to determine the position of the center of gravity of an optical beam and can be used with the assembly according to the present invention. The sensitivity of the assembly regarding the determination of the height and the inclination of the inspected surface, however, essentially depends on the spacial resolution during determination of the center of gravity of the beam.

A retroreflector, a retro reflection sheet or another suitable reflector is provided in a particularly preferred embodiment of the invention to direct the radiation generated by the radiation source several times over the inspected surface. Two or three reflecting surfaces or a total reflecting prism can be provided as a retroreflector. Thereby, the resolution of the assembly can be increased. The retroreflector is positioned at the side opposing the radiation source.

Retroreflectors are assemblies with two or three reflecting surfaces reflecting light back to the direction of incidence. Contrary to simple reflectors, such as, for example, a plane mirror, a parallel shift is generated. The reflecting surfaces can be formed by mirrors as well as by prisms with total reflection. Typically, the reflecting surfaces are perpendicular to each other. A retroreflector with only two surfaces operates retro reflectively only in one plane perpendicular to the two mirror planes. The reflecting surfaces of a retroreflector with three surfaces are arranged in the form of an edge of a cube. Thereby the surfaces generate retro reflection in the entire spacial angular range of incidence. In order to increase the sensitivity of the assembly according to the present invention a retroreflector with two surfaces can already be effectively used as long as the reflecting surfaces are perpendicular to the vertical plane of the emitted beam of the radiation source.

The beams still have a comparatively small distance after the first reflection at the sample. If the beams are reflected back to the inspected surface by the retroreflector and reflected again the returning beams will have a larger distance at the detector. Thereby, the sensitivity of the assembly is doubled compared to simple reflection. It is understood, that further retroreflectors can be used to send the beam several times back and forth and thereby reflect several times at the inspected surface. Thereby, the resolution is further increased. It is not necessary that the reflection locations on the inspected surface are identical. The reflection locations can be selected by choosing angles different from 90° between the mirror surfaces of the retroreflector.

In a further modification of the present invention the detector surface is positioned in such a way that the detected radiation forms an angle with the surface normal of the detector surface. Thereby, the resolution and the sensitivity of the assembly can be further increased. The smaller the angle of the reflected beam incident on the detector the more the height position signal or the signal of the inclination of the sample is increased. Since the imaging of the beam on an inclined detector area causes an increased ellipticity of the beam profile it is advantageous if the beam profile is specifically adapted at the radiation source by suitable optical elements. If the inspected surface is parallel directed to the direction of the detector surface, the height resolution relative to the detector surface position perpendicular to the reflected beam can be increased by a factor 3 with an angle of incidence of, for example, 20° relative to the inspected surface. The increase of the sensitivity is already a factor 4 at 15°.

It may be provided that the radiation source generates polarized light and an analyzer is provided before the detector. Also, modulation means for modulating the intensity of the radiation source can be provided. Thereby, the assembly, in particular the inspection measurement can be made more insensitive regarding stray light and corrected for outside influences. Such methods are known from the technique of reflection light scanners and can be combined also with the present invention.

In an embodiment of the assembly a very stiff connection of the radiation source and the detector as well as the inspection system is advantageous. This can be achieved by the selection of high profile diameters.

The assembly can be used for an inspection method for inspecting an at least partially reflecting surface of a wafer or another object with an inspection assembly positioned spaced apart in the range before the inspected surface, the method used for determining the distance and/or inclination of the surface with respect to the inspection assembly, characterized by the steps of (a) illuminating the inspected surface with radiation from a radiation source at an angle;
(b) detecting radiation from the radiation source reflected by the inspected surface with a spatially resolving detector; wherein the radiation source and the detector are positioned outside the range required for the inspection between the inspection assembly and the inspected surface; and
(c) determining the height and/or inclination from the position of the reflected radiation on the detector and/or controlling the height and/or inclination according to the position of the reflected radiation on the detector.

Further modifications of the invention are subject matter of the subclaims. An embodiment is described below in greater detail with reference to the accompanying drawings.

DESCRIPTION OF THE EMBODIMENTS

Figure 1:
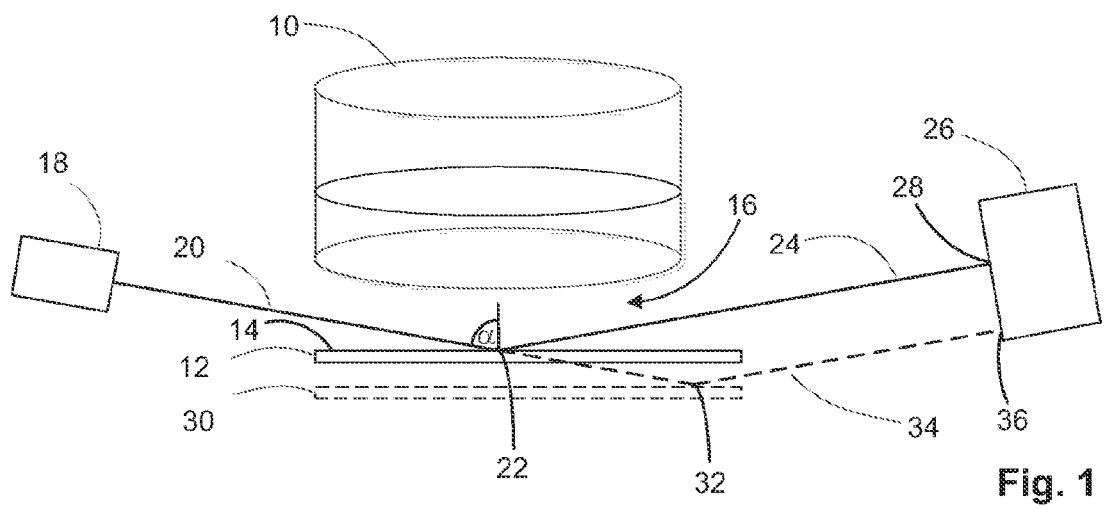
FIG. 1 is a schematic side view of an inspection assembly with an inspected object illustrating the effects of a height shift.

FIG. 1 shows an inspection assembly for wafers 12 generally denoted with numeral 10. The inspection assembly 10 uses one of the methods ellipsometry, scatterometry, reflectometry, optical inspection, inspection with any other electromagnetic radiation and ultrasound sensorics. The inspection assembly can, however, also apply a photolithographic method.

The wafer 12 lays on a holder which is not shown here. The holder is designed in such a way that the wafer can be moved in height and also inclined and is equipped with a suitable movement control. Such distance corresponds to the height of the wafer in the present assembly with horizontally positioned wafer. Also, an inclination of the surface 14 can be defined, for example relative to the horizontal plane. The above methods of the inspection assembly are sensitive regarding height and inclination of the wafer.

Therefore, a measuring assembly for determining the height and inclination of the surface is provided in the present embodiment. The measuring assembly comprises a diode laser 18 as a radiation source. The diode laser 18 emits a well collimated laser beam 20.

The laser beam 20 is incident on the surface 14 of the wafer 12 under a flat angle. The angle α of the laser beam formed with the surface normal of the surface 14 is in the range of 80°. It can be recognized that the beam 20 passes well through the space 16 between the inspection assembly 10 and the wafer surface 14 with such an angle. The laser diode 18 with the corresponding control- and supply units is far outside of the range 16.

The wafer surface 14 is reflecting. The laser beam 20 is, therefore, reflected at a point 22 of the surface 14. The point of incidence is selected in such a way that the inspection assembly 10 is not interfered with with its tasks, i.e. slightly remote from the actual point of inspection. Outside of the range 16 the reflected beam designated with numeral 24 is incident on a CCD camera 26 having a plurality of image points which are arranged in lines and columns.

If the assembly is well adjusted and has a horizontal wafer surface 14 where the wafer surface is exactly in the focus of the inspection assembly 10 the reflected laser beam 24 is incident about in the middle of the CCD camera 26. This point is designated with numeral 28 and describes a set value for the point of incidence.

There are cases, where the wafer has a different distance to the inspection assembly. The laser beam 24 will then not be incident on point 28 on the detector. FIG. 1 illustrates the case where the distance is slightly larger and the wafer assumes the position designated with numeral 30. It can be recognized that the laser beam 20 is incident on the wafer surface 14 only at point 32. The reflected beam 34 shown in dashed lines is incident on the detector at point 36. The deviation from the focus position of the wafer 12 can be derived from the deviation of the actual position at point 36 and the set position at point 28. In the present embodiment the holder is controlled in such a way that the wafer will assume its set position and the varied beam 24 is incident at point 28 on the detector 26.

Figure 2:
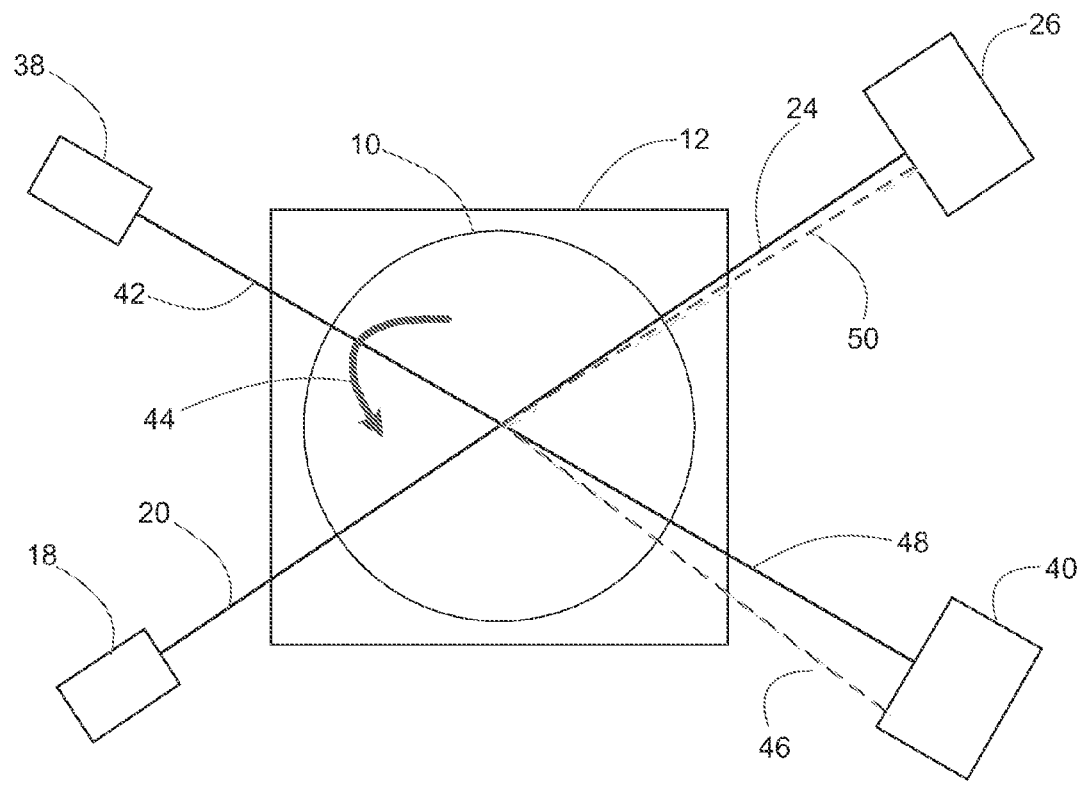
FIG. 2 is a top view of the assembly of FIG. 1.

FIG. 2 shows a top view of the assembly of FIG. 1. It can be recognized that two diode lasers 18 and 38 are provided with corresponding CCD-cameras 26 and 40. The diode lasers 18 and 38 are arranged in such a way that the laser beams 20 and 42 will cross in the measuring range. It is not necessary that both beams cross at exactly the same point on the wafer surface, nor is it necessary that the angles of incidence are exactly the same. Using two laser beams 20 and 42 the inclination of the wafer surface 14 can be determined in addition to the distance.

In the present embodiment the case is illustrated in FIG. 2, where the wafer surface 14 is inclined about an axis which corresponds to the projection of the connecting axis between laser diode 38 and CCD-camera 40 on the wafer surface 14. This is represented by arrow 44. Due to the inclination both laser beams are deflected in a different way. The deviation of the set value is larger at detector 40 than at detector 26. From the deviation the inclination against the horizontal plane can be determined. As with the distance, the holder can be controlled in such a way that the wafer will assume a set position.

Figure 3:
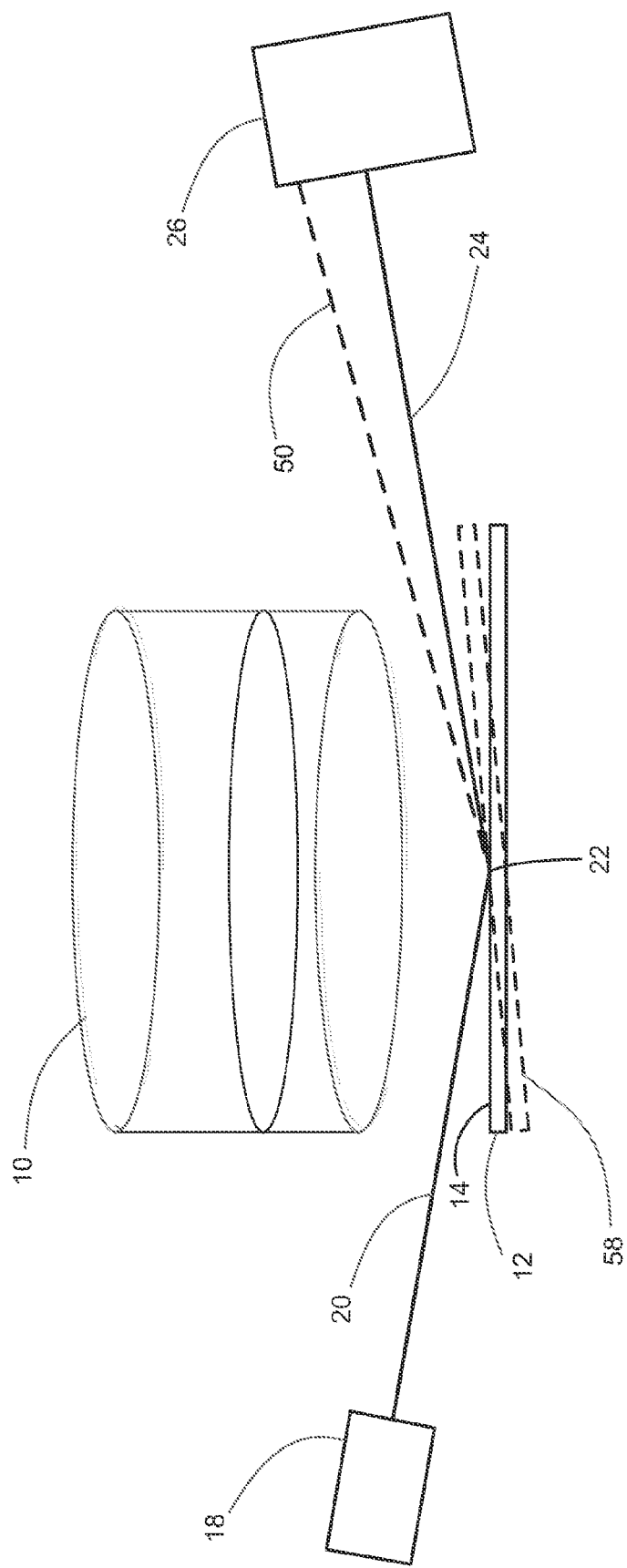
FIG. 3 shows the assembly of FIG. 1 illustrating the effects of an inclination of the inspected object.

FIG. 3 shows the case from the side where the wafer 58 is inclined against a horizontal wafer 12. The inclined wafer 58 is shown in dashed lines. It can be seen that the laser beam 20 is reflected at the same position 22 at the wafer surface 14, but with a different angle. This causes the reflected beam 50 to be incident further up on the detector 26. Accordingly, an inclination in a different direction will cause the beam 50 to be incident further down on the detector 26.

Figure 4:
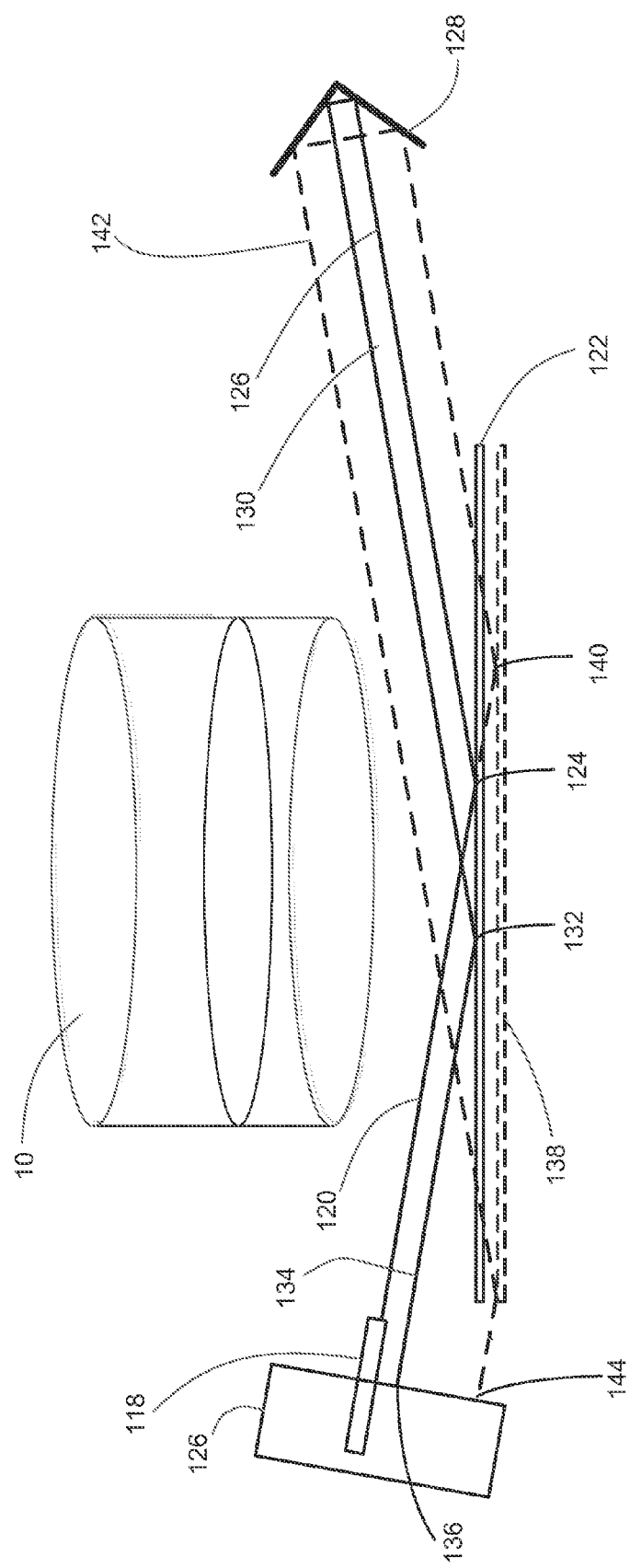
FIG. 4 shows an assembly similar to the one in FIG. 1, where an increased resolution is achieved by the use of a retroreflector.

FIG. 4 shows an assembly according to an alternative embodiment with increased resolution. The assembly is identical to the assembly shown in FIG. 1. The detector 126, however, is not arranged opposite to the radiation source 118, but on the same side. The beam 120 generated by the laser diode 118 is reflected at point 124 on the wafer surface 122. The reflected beam 126 is incident on a retroreflector 128 with two plane mirrors. There, the beam 126 is reflected back with a shift. The reflected beam 130 is incident on the wafer surface 122 again at point 132. Due to the shift of the beam the point 132 is at a different location than the point 124. The beam 134 reflected again at the wafer surface is finally incident on the detector 126 at point 136.

If the wafer surface 122 is, for example, further down, the path of rays will change. The wafer surface with larger distance is shown in dashed lines in FIG. 4 and designated with numeral 138. It can be recognized that the beam 120 is reflected at a different point 140 of the wafer surface. After passing the retroreflector 128 the beam 142 is incident on the wafer again and at point 144 on the detector. It can easily be understood, that the shift of the point of incidence 136 on the detector is larger with retroreflector 128 than without. In such a way the resolution of the measuring assembly and thereby the sensitivity is increased.

Figure 5:
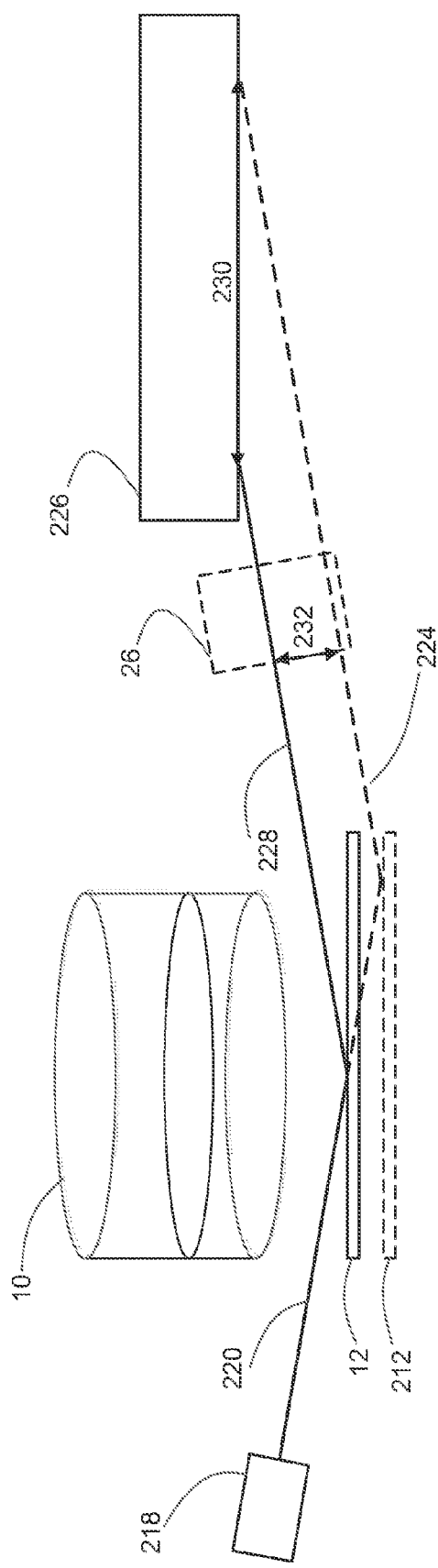
FIG. 5 shows an assembly similar to the one in FIG. 1, where an increased resolution is achieved by inclination of the detector.

FIG. 5 shows an embodiment where the sensitivity of the assembly is increased by inclining the detector 226 in such a way that an angle is formed between the surface normal of the detector surface and the incident beam 228. The more flat the beam is incident on the detector surface the more the signal of inclination of the inspected surface is increased. It can be recognized that the distance between the points of incidence on the detector and the beams 224 and 228 with inclined detector—here designated with numeral 230—is larger than the distance 232 with the perpendicular arranged detector 26 shown here in dashed lines.

Since the image of the beam 220 or 228, respectively, on an inclined detector surface causes an increased ellipticity of the beam profile, a suitable optical arrangement (not shown) is provided before the laser diode for beam adaptation.

The invention claimed is:

1. An assembly for inspecting a wafer or other object, said wafer or said object having a surface which is at least partly reflecting, said assembly comprising:
   (a) a support for supporting said wafer or said object;

(b) an inspection assembly requiring an inspection space between said inspection assembly and said surface which is without devices which would interfere with radiation traveling through said inspection space, said inspection assembly positioned spaced apart before said wafer or said object thereby defining a distance between said surface and said inspection assembly and an inclination of said surface with respect to said inspection assembly, and defining said inspection space between said inspection assembly and said surface which is necessary for the inspection; and (c) a measuring assembly separate and apart from said inspection assembly for simultaneously determining said distance and said inclination of said surface;

(d) wherein said measuring assembly comprises a first radiation source emitting radiation which is directed towards said surface defining an angle between said radiation and said surface; and (e) a first space-resolving detector for detection of said radiation from said first radiation source reflected by said surface, wherein (f) said first radiation source and said first space-resolving detector are positioned outside a said inspection space between said inspection assembly and said surface, and wherein (g) an additional radiation source emitting radiation with a corresponding additional, space-resolving detector is provided at a different position in a crossing arrangement where said radiation emitted by said first radiation source has a different direction than said radiation emitted by said additional radiation source.

2. The assembly of claim 1, and wherein said radiation of said first and additional radiation source is incident at a position on said detector and means are provided for determining said distance and said inclination of said surface from said position.

3. The assembly of claim 1, and wherein said support or said wafer or said object in said support are moveably mounted and the inclination and/or distance of said surface is adapted to be adjusted in such a way that a desired position of said reflected radiation on said detectors is achieved.

4. The assembly of claim 1, and wherein said angle at which said radiation is directed from said radiation sources to said surface is in a range between 45° and 85° relative to a surface normal of said surface.

5. The assembly of claim 1, and wherein said radiation sources are formed by a laser diodes or LEDs each equipped with a collimator optics or by radiation sources with an extended wavelength spectrum adapted to detect interferences at repeating structures of said surface.

6. The assembly of claim 1, and wherein said detectors are Charge-Coupled-Devices (CCD), a CMOS or another array detectors with high spacial resolution or that said detectors comprise position sensitive photodiodes or quadrant diodes.

7. The assembly of claim 1, and wherein a retroreflector, a retro reflection sheet or another suitable reflector is provided to direct said radiation generated by said radiation sources several times over said inspected surface.

8. The assembly of claim 7, and wherein a retroreflector with two or three reflecting surfaces or a total reflecting prism is provided.

9. The assembly of claim 1, and wherein said detectors have a detector surface which is positioned in such a way that said radiation incident on said detector forms an angle with said detector surface.

10. The assembly of claim 1, and wherein said radiation sources generate polarized light and analyzers are provided before said detector.

11. The assembly of claim 1 and wherein said radiation has an intensity and the assembly further comprising modulation means for modulating said intensity of said radiation source.

12. An inspection method for inspecting a wafer or other object, said wafer or said object having a surface which is at least partly reflecting, with an inspection assembly requiring a space between said inspection assembly and said surface which is without devices which would interfere with radiation traveling through said inspection space, and said inspection assembly is positioned spaced apart before said wafer or said object thereby defining a distance between said surface and said inspection assembly and an inclination of said surface with respect to said inspection assembly, and defining said inspection space between said inspection assembly and said surface which is necessary for the inspection, the method used for determining said distance and said inclination, with the steps of (a) illuminating said surface at an angle with radiation from a first radiation source separate and apart from the inspection assembly and positioned outside said inspection space;

(b) detecting radiation from said first radiation source reflected by said surface with a first spatially resolving detector separate and apart from the inspection assembly and positioned outside said inspection space;

(c) simultaneously illuminating said surface at an angle with radiation from a second radiation source at a different position than the first radiation source and separate and apart from the inspection assembly and positioned outside said inspection space;

(d) detecting radiation from said second radiation source reflected by said surface with a second spatially resolving detector separate and apart from the inspection assembly and positioned outside said inspection space; and (e) simultaneously determining said height and said inclination from the positions of said reflected radiation on said detectors and/or controlling said height and said inclination according to said position of said reflected radiation on said detectors.

* * * * *